(12) United States Patent
Lenz et al.

(10) Patent No.: US 8,926,709 B2
(45) Date of Patent: Jan. 6, 2015

(54) STRUCTURES FOR USE IN ORTHOPAEDIC IMPLANT FIXATION AND METHODS OF INSTALLATION ONTO A BONE

(75) Inventors: Nathaniel Milton Lenz, Germantown, TN (US); Zachary Christopher Wilkinson, Germantown, TN (US)

(73) Assignee: Smith & Nephew, Inc., Memphis, TN (US)

(*) Notice: Subject to any disclaimer, the term of this patent is extended or adjusted under 35 U.S.C. 154(b) by 282 days.

(21) Appl. No.: 13/207,888

(22) Filed: Aug. 11, 2011

(65) Prior Publication Data

US 2012/0041566 A1 Feb. 16, 2012

Related U.S. Application Data

(60) Provisional application No. 61/372,902, filed on Aug. 12, 2010.

(51) Int. Cl.
*A61F 2/38* (2006.01)
*A61F 2/36* (2006.01)
*A61F 2/30* (2006.01)

(52) U.S. Cl.
CPC .......... *A61F 2/38* (2013.01); *A61F 2/3601* (2013.01); *A61F 2/30721* (2013.01); *A61F 2/3859* (2013.01); *A61F 2/389* (2013.01); *A61F 2002/3021* (2013.01); *A61F 2002/30828* (2013.01); *A61F 2002/30878* (2013.01); *A61F 2002/30879* (2013.01); *A61F 2002/30892* (2013.01); *A61F 2002/30897* (2013.01)
USPC .................. 623/23.42; 623/20.3; 623/20.36

(58) Field of Classification Search
CPC .............. A61F 2/3601; A61F 2/3859; A61F 2002/3021; A61F 2002/30878
USPC .......... 623/20.14, 20.21, 20.31, 20.35, 20.36, 623/23.42, 22.37, 23.44, 23.11, 23.12
See application file for complete search history.

(56) References Cited

U.S. PATENT DOCUMENTS 3,748,662 A 7/1973 Helfet
3,774,244 A 11/1973 Walker
(Continued)

FOREIGN PATENT DOCUMENTS

EP 0 121 142 10/1984
EP 0 189 253 7/1986
(Continued)

OTHER PUBLICATIONS

"European Hospital . . . The European Forum for Those in the Business of Making Healthcare Work," 12(5/03):1-24 (Oct./Nov. 2003).
(Continued)

*Primary Examiner* — David H Willse
*Assistant Examiner* — Javier Blanco
(74) *Attorney, Agent, or Firm* — Krieg DeVault LLP

(57) ABSTRACT

An orthopaedic implant including a base portion and first and second transverse portions extending transversely from the base portion to thereby define an inner region of the implant sized for receipt of an end portion of a bone therein. The implant further includes at least one anchor structure projecting from the base portion and sized and configured for receipt within an opening formed in the end portion of the bone. The anchor structure extends along a longitudinal axis and includes a proximal end attached to the base portion and an opposite distal end, and further includes a tapered outer surface that inwardly tapers in a proximal-to-distal direction along the longitudinal axis. In one embodiment, the anchor structure also includes one or more grooves extending into the tapered outer surface, with a flowable material positioned about at least a portion of the tapered outer surface and positioned within the grooves, and with the flowable material configured to cure to a hardened state.

30 Claims, 7 Drawing Sheets

(56) References Cited

U.S. PATENT DOCUMENTS

| | | | |
|---|---|---|---|
| 3,798,679 A | 3/1974 | Ewald | |
| 3,816,855 A | 6/1974 | Saleh | |
| 3,878,566 A * | 4/1975 | Bechtol | 623/20.19 |
| 3,958,278 A | 5/1976 | Lee et al. | |
| 4,016,606 A | 4/1977 | Murray et al. | |
| 4,178,641 A | 12/1979 | Grundei et al. | |
| 4,207,627 A | 6/1980 | Cloutier | |
| 4,213,209 A | 7/1980 | Insall et al. | |
| 4,249,270 A | 2/1981 | Bahler et al. | |
| 4,340,978 A | 7/1982 | Buechel et al. | |
| 4,353,135 A | 10/1982 | Forte et al. | |
| 4,358,859 A | 11/1982 | Schurman et al. | |
| 4,474,177 A | 10/1984 | Whiteside | |
| 4,524,766 A | 6/1985 | Petersen | |
| 4,568,348 A | 2/1986 | Johnson et al. | |
| 4,586,933 A | 5/1986 | Shoji et al. | |
| 4,653,488 A | 3/1987 | Kenna et al. | |
| 4,659,331 A | 4/1987 | Matthews et al. | |
| 4,662,889 A * | 5/1987 | Zichner et al. | 623/20.26 |
| 4,703,751 A | 11/1987 | Pohl | |
| 4,711,639 A | 12/1987 | Grundel | |
| 4,714,472 A | 12/1987 | Averill et al. | |
| 4,714,473 A | 12/1987 | Bloebaum | |
| 4,721,104 A | 1/1988 | Kaufman et al. | |
| 4,722,330 A | 2/1988 | Russell et al. | |
| 4,731,086 A | 3/1988 | Whiteside et al. | |
| 4,770,663 A | 9/1988 | Hanslik et al. | |
| 4,787,383 A | 11/1988 | Kenna | |
| 4,822,365 A | 4/1989 | Walker et al. | |
| 4,834,758 A | 5/1989 | Lane et al. | |
| 4,892,547 A | 1/1990 | Brown | |
| 4,926,847 A | 5/1990 | Luckman | |
| 4,936,853 A | 6/1990 | Fabian et al. | |
| 4,938,769 A | 7/1990 | Shaw | |
| 4,944,757 A | 7/1990 | Martinez et al. | |
| 4,950,298 A | 8/1990 | Gustilo et al. | |
| 4,963,152 A | 10/1990 | Hofmann et al. | |
| 4,979,949 A | 12/1990 | Matsen, III et al. | |
| 5,002,547 A | 3/1991 | Poggie et al. | |
| 5,007,933 A | 4/1991 | Sidebotham et al. | |
| 5,021,061 A | 6/1991 | Wevers et al. | |
| 5,032,134 A | 7/1991 | Lindwer | |
| 5,035,699 A | 7/1991 | Coates | |
| 5,053,037 A | 10/1991 | Lackey | |
| 5,062,852 A | 11/1991 | Dorr et al. | |
| 5,080,675 A | 1/1992 | Lawes et al. | |
| 5,092,869 A | 3/1992 | Waldron | |
| 5,098,436 A | 3/1992 | Ferrante et al. | |
| 5,100,409 A | 3/1992 | Coates | |
| 5,116,375 A | 5/1992 | Hofmann | |
| 5,122,144 A | 6/1992 | Bert et al. | |
| 5,129,909 A | 7/1992 | Sutherland | |
| 5,133,758 A | 7/1992 | Hollister | |
| 5,133,759 A | 7/1992 | Turner | |
| 5,147,405 A | 9/1992 | Van Zile et al. | |
| 5,201,881 A | 4/1993 | Evans | |
| 5,203,807 A | 4/1993 | Evans et al. | |
| 5,219,362 A | 6/1993 | Tuke et al. | |
| 5,226,916 A | 7/1993 | Goodfellow et al. | |
| 5,228,459 A | 7/1993 | Caspari et al. | |
| 5,234,433 A | 8/1993 | Bert et al. | |
| 5,236,432 A | 8/1993 | Matsen et al. | |
| 5,236,461 A | 8/1993 | Forte | |
| 5,250,050 A | 10/1993 | Poggie et al. | |
| 5,263,498 A | 11/1993 | Caspari et al. | |
| 5,282,803 A | 2/1994 | Lackey | |
| 5,282,867 A | 2/1994 | Mikhall | |
| 5,304,181 A | 4/1994 | Caspari et al. | |
| 5,312,411 A * | 5/1994 | Steele et al. | 606/88 |
| 5,314,482 A | 5/1994 | Goodfellow et al. | |
| 5,326,358 A | 7/1994 | Aubriot et al. | |
| 5,330,533 A | 7/1994 | Walker | |
| 5,330,534 A | 7/1994 | Herrington et al. | |
| 5,358,527 A | 10/1994 | Forte | |
| 5,358,529 A | 10/1994 | Davidson | |
| 5,358,531 A | 10/1994 | Goodfellow et al. | |
| 5,370,699 A | 12/1994 | Hood et al. | |
| 5,370,701 A | 12/1994 | Finn | |
| 5,413,604 A | 5/1995 | Hodge | |
| 5,417,694 A | 5/1995 | Marik et al. | |
| 5,454,816 A | 10/1995 | Ashby | |
| 5,480,446 A | 1/1996 | Goodfellow et al. | |
| 5,514,143 A | 5/1996 | Bonutti et al. | |
| 5,520,695 A | 5/1996 | Luckman | |
| 5,549,684 A | 8/1996 | Amino et al. | |
| 5,549,688 A | 8/1996 | Ries et al. | |
| 5,571,194 A | 11/1996 | Gabriel | |
| 5,609,645 A | 3/1997 | Vinciguerra | |
| 5,611,802 A | 3/1997 | Samuelson et al. | |
| 5,639,279 A | 6/1997 | Burkinshaw et al. | |
| 5,667,511 A | 9/1997 | Vendrely et al. | |
| 5,681,354 A | 10/1997 | Eckhoff | |
| 5,682,886 A | 11/1997 | Delp et al. | |
| 5,690,635 A | 11/1997 | Matsen et al. | |
| 5,690,637 A | 11/1997 | Wen et al. | |
| 5,702,458 A | 12/1997 | Burstein et al. | |
| 5,723,016 A | 3/1998 | Minns et al. | |
| 5,728,162 A | 3/1998 | Eckhoff | |
| 5,749,876 A | 5/1998 | Duvillier et al. | |
| 5,755,801 A | 5/1998 | Walker et al. | |
| 5,755,803 A | 5/1998 | Haines et al. | |
| 5,755,804 A | 5/1998 | Schmotzer et al. | |
| 5,766,255 A * | 6/1998 | Slamin et al. | 623/20.15 |
| 5,766,257 A | 6/1998 | Goodman et al. | |
| 5,776,200 A | 7/1998 | Johnson et al. | |
| 5,782,921 A | 7/1998 | Colleran et al. | |
| 5,782,925 A | 7/1998 | Collazo et al. | |
| 5,800,552 A | 9/1998 | Forte | |
| 5,810,827 A | 9/1998 | Haines et al. | |
| 5,824,100 A | 10/1998 | Kester et al. | |
| 5,824,102 A | 10/1998 | Buscayret | |
| 5,824,105 A | 10/1998 | Ries et al. | |
| 5,871,545 A | 2/1999 | Goodfellow et al. | |
| 5,871,546 A | 2/1999 | Colleran et al. | |
| 5,879,392 A | 3/1999 | McMinn | |
| 5,906,643 A | 5/1999 | Walker | |
| 5,935,173 A | 8/1999 | Roger et al. | |
| 5,954,770 A | 9/1999 | Schmotzer et al. | |
| 5,997,577 A | 12/1999 | Herrington et al. | |
| 6,039,764 A | 3/2000 | Pottenger et al. | |
| 6,059,788 A | 5/2000 | Katz | |
| 6,068,658 A | 5/2000 | Insall et al. | |
| 6,080,195 A | 6/2000 | Colleran et al. | |
| 6,099,570 A | 8/2000 | Livet et al. | |
| 6,120,543 A | 9/2000 | Kubein-Meesenburg et al. | |
| 6,132,468 A | 10/2000 | Mansmann | |
| 6,139,581 A | 10/2000 | Engh et al. | |
| 6,165,221 A | 12/2000 | Schmotzer | |
| 6,165,223 A | 12/2000 | Metzger et al. | |
| 6,171,340 B1 | 1/2001 | McDowell | |
| 6,197,064 B1 | 3/2001 | Haines et al. | |
| 6,203,576 B1 | 3/2001 | Afriat et al. | |
| 6,206,926 B1 | 3/2001 | Pappas | |
| 6,210,443 B1 | 4/2001 | Marceaux et al. | |
| 6,235,060 B1 | 5/2001 | Kubein-Meesenburg et al. | |
| 6,264,697 B1 | 7/2001 | Walker | |
| 6,306,172 B1 | 10/2001 | O'Neil et al. | |
| 6,325,828 B1 | 12/2001 | Dennis et al. | |
| 6,361,564 B1 | 3/2002 | Marceaux et al. | |
| 6,379,388 B1 | 4/2002 | Ensign et al. | |
| 6,406,497 B2 | 6/2002 | Takei | |
| 6,413,279 B1 | 7/2002 | Metzger et al. | |
| 6,436,145 B1 | 8/2002 | Miller | |
| 6,443,991 B1 | 9/2002 | Running | |
| 6,475,241 B2 | 11/2002 | Pappas | |
| 6,485,519 B2 | 11/2002 | Meyers et al. | |
| 6,491,726 B2 | 12/2002 | Pappas | |
| 6,500,208 B1 | 12/2002 | Metzger et al. | |
| 6,506,215 B1 | 1/2003 | Letot et al. | |
| 6,554,838 B2 | 4/2003 | McGovern et al. | |
| 6,569,202 B2 | 5/2003 | Whiteside | |
| 6,575,980 B1 | 6/2003 | Robie et al. | |
| 6,589,283 B1 | 7/2003 | Metzger et al. | |
| 6,620,198 B2 | 9/2003 | Burstein et al. | |

(56) References Cited

U.S. PATENT DOCUMENTS

| | | |
|---|---|---|
| 6,623,526 B1 | 9/2003 | Lloyd |
| 6,645,251 B2 | 11/2003 | Salehi et al. |
| 6,695,848 B2 | 2/2004 | Haines |
| 6,702,821 B2 | 3/2004 | Bonutti |
| 6,730,128 B2 | 5/2004 | Burstein |
| 6,755,864 B1 | 6/2004 | Brack et al. |
| 6,764,516 B2 | 7/2004 | Pappas |
| 6,770,097 B2 | 8/2004 | Leclercq |
| 6,770,099 B2 | 8/2004 | Andriacchi et al. |
| 6,773,461 B2 | 8/2004 | Meyers et al. |
| 6,811,568 B2 | 11/2004 | Minamikawa |
| 6,827,723 B2 | 12/2004 | Carson |
| 6,846,329 B2 | 1/2005 | McMinn |
| 6,866,683 B2 | 3/2005 | Gerbec et al. |
| 6,866,684 B2 | 3/2005 | Fell et al. |
| 6,887,276 B2 | 5/2005 | Gerbec et al. |
| 6,911,044 B2 | 6/2005 | Fell et al. |
| 6,916,324 B2 | 7/2005 | Sanford et al. |
| 6,916,340 B2 | 7/2005 | Metzger et al. |
| 7,018,418 B2 | 3/2006 | Amrich et al. |
| 7,048,741 B2 | 5/2006 | Swanson |
| 7,077,867 B1 | 7/2006 | Pope et al. |
| 7,104,996 B2 | 9/2006 | Bonutti |
| 7,141,053 B2 | 11/2006 | Rosa et al. |
| 7,160,330 B2 | 1/2007 | Axelson, Jr. et al. |
| 7,175,667 B2 * | 2/2007 | Saunders et al. ............ 623/21.19 |
| 7,326,252 B2 | 2/2008 | Otto et al. |
| 7,371,240 B2 | 5/2008 | Pinczewski et al. |
| 7,922,771 B2 | 4/2011 | Otto et al. |
| 2001/0018615 A1 | 8/2001 | Biegun et al. |
| 2002/0055784 A1 | 5/2002 | Burstein et al. |
| 2002/0103541 A1 | 8/2002 | Meyers et al. |
| 2002/0107576 A1 | 8/2002 | Meyers et al. |
| 2002/0120340 A1 | 8/2002 | Metzger et al. |
| 2002/0161447 A1 | 10/2002 | Salehi et al. |
| 2003/0009228 A1 | 1/2003 | Meyers et al. |
| 2003/0009230 A1 | 1/2003 | Gundlapalli et al. |
| 2003/0055501 A1 | 3/2003 | Fell et al. |
| 2003/0055509 A1 | 3/2003 | McCue et al. |
| 2003/0060882 A1 | 3/2003 | Fell et al. |
| 2003/0060883 A1 | 3/2003 | Fell et al. |
| 2003/0060884 A1 | 3/2003 | Fell et al. |
| 2003/0060885 A1 | 3/2003 | Fell et al. |
| 2003/0069591 A1 | 4/2003 | Carson et al. |
| 2003/0093156 A1 | 5/2003 | Metzger et al. |
| 2003/0100953 A1 | 5/2003 | Rosa et al. |
| 2003/0153977 A1 | 8/2003 | Suguro et al. |
| 2003/0153979 A1 | 8/2003 | Hughes et al. |
| 2003/0163201 A1 | 8/2003 | McMinn |
| 2003/0220697 A1 | 11/2003 | Justin et al. |
| 2004/0006393 A1 | 1/2004 | Burkinshaw |
| 2004/0030387 A1 | 2/2004 | Landry et al. |
| 2004/0034432 A1 | 2/2004 | Hughes et al. |
| 2004/0044414 A1 | 3/2004 | Nowakowski |
| 2004/0102852 A1 | 5/2004 | Johnson et al. |
| 2004/0122522 A1 | 6/2004 | Kubein-Meesenburg et al. |
| 2004/0143339 A1 | 7/2004 | Axelson, Jr. et al. |
| 2004/0153066 A1 | 8/2004 | Coon et al. |
| 2004/0153164 A1 | 8/2004 | Sanford et al. |
| 2004/0162620 A1 | 8/2004 | Wyss |
| 2004/0193280 A1 | 9/2004 | Webster et al. |
| 2004/0199249 A1 | 10/2004 | Fell |
| 2004/0199250 A1 | 10/2004 | Fell |
| 2004/0204766 A1 | 10/2004 | Siebel |
| 2004/0249467 A1 | 12/2004 | Meyers et al. |
| 2004/0249468 A1 | 12/2004 | Suguro et al. |
| 2004/0267363 A1 | 12/2004 | Fell et al. |
| 2005/0021147 A1 | 1/2005 | Tarabichi |
| 2005/0033424 A1 | 2/2005 | Fell |
| 2005/0055102 A1 | 3/2005 | Tornier et al. |
| 2005/0107886 A1 | 5/2005 | Crabtree et al. |
| 2005/0143832 A1 | 6/2005 | Carson |
| 2005/0171604 A1 | 8/2005 | Michalow |
| 2005/0209701 A1 | 9/2005 | Suguro et al. |
| 2005/0267363 A1 | 12/2005 | Duchon et al. |
| 2006/0015109 A1 | 1/2006 | Haines |
| 2006/0015115 A1 | 1/2006 | Haines |
| 2006/0015116 A1 | 1/2006 | Haines |
| 2006/0015117 A1 | 1/2006 | Haines |
| 2006/0030853 A1 | 2/2006 | Haines |
| 2006/0030854 A1 | 2/2006 | Haines |
| 2006/0030855 A1 | 2/2006 | Haines |
| 2006/0030944 A1 | 2/2006 | Haines |
| 2006/0052875 A1 | 3/2006 | Bernero et al. |
| 2006/0058882 A1 | 3/2006 | Haines |
| 2007/0078517 A1 | 4/2007 | Engh et al. |
| 2007/0118229 A1 * | 5/2007 | Bergin et al. .............. 623/23.31 |
| 2008/0119940 A1 * | 5/2008 | Otto et al. .................. 623/20.31 |
| 2009/0062926 A1 | 3/2009 | Wyss |
| 2009/0076514 A1 | 3/2009 | Haines |
| 2009/0270994 A1 | 10/2009 | Schaefer et al. |
| 2010/0100192 A1 | 4/2010 | Haines et al. |
| 2010/0185203 A1 | 7/2010 | Haines |

FOREIGN PATENT DOCUMENTS

| | | |
|---|---|---|
| EP | 0 243 109 | 10/1987 |
| EP | 0 327 249 | 8/1989 |
| EP | 0 349 173 | 1/1990 |
| EP | 0 380 451 | 1/1990 |
| EP | 0 466 659 | 1/1992 |
| EP | 0 538 153 | 4/1993 |
| EP | 0 555 003 | 8/1993 |
| EP | 0 916 321 | 5/1999 |
| EP | 0 923 916 | 6/1999 |
| EP | 0 941 719 | 9/1999 |
| EP | 0 970 667 | 1/2000 |
| EP | 0 988 840 | 3/2000 |
| EP | 1 477 143 | 11/2004 |
| EP | 1 484 036 | 12/2004 |
| FR | 2621243 A1 * | 4/1989 |
| FR | 2 635 675 | 3/1990 |
| FR | 2 664 157 | 1/1992 |
| FR | 2 701 387 | 8/1994 |
| FR | 2 710 258 | 3/1995 |
| FR | 2 760 352 | 9/1998 |
| FR | 2803191 A1 * | 7/2001 |
| GB | 0 296 443 | 8/1928 |
| GB | 1 409 150 | 10/1975 |
| GB | 2 007 980 | 7/1982 |
| GB | 2 296 443 | 7/1996 |
| GB | 2 324 249 | 10/1998 |
| GB | 2 335 145 | 9/1999 |
| JP | 61-170453 | 8/1986 |
| JP | 62-133948 | 6/1987 |
| JP | 62-254750 | 11/1987 |
| JP | 02-246971 | 10/1990 |
| JP | 04-297254 | 10/1992 |
| JP | 06-237941 | 8/1994 |
| RU | 2121319 | 11/1998 |
| WO | WO 91/10408 | 7/1991 |
| WO | WO 93/25157 | 12/1993 |
| WO | WO 94/05212 | 3/1994 |
| WO | WO 94/09730 | 5/1994 |
| WO | WO 94/22397 | 10/1994 |
| WO | WO 96/01588 | 1/1996 |
| WO | WO 97/29703 | 8/1997 |
| WO | WO 97/29704 | 8/1997 |
| WO | WO 98/20817 | 5/1998 |
| WO | WO 99/27872 | 6/1999 |
| WO | WO 99/30649 | 6/1999 |
| WO | WO 01/13825 | 3/2001 |
| WO | WO 2004/100839 | 11/2004 |
| WO | WO 2007054553 A1 * | 5/2007 |

OTHER PUBLICATIONS

Whiteside Ortholoc Total Knee System: Surgical Procedure, Dow Corning Wright, pp. WMT000001-WMT000040, Jun. 1985.

Zimmer, Insall/Burstein II, Constrained Condylar: Modular Knee System, Surgical Technique, Copyright 1989.

Zimmer, The Miller/Galante Advantage: Total Knee System, pp. ZH000159653-ZH000159668.

(56) References Cited

OTHER PUBLICATIONS

Whiteside Ortholoc Total Knee System, Dow Corning Wright, pp. ZH000109679-ZH000109690.

Zimmer, Insall/Burnstein II, Modular Knee System, Surgical Technique, pp. ZH000109691-ZH000109710.

Exhibits 4, 5 and 8 from *Hudson Surgical Design, Inc.* v. *Zimmer Holdings, Inc., Zimmer Inc.*, Rush System for Health and Rush University Medical Center, Hudson Surgical Design, Inc.'s Opening Brief on Claim Construction, Case No. 1:08-cv-01566, Civil Action No. 08C1566, Document No. 83, filed Nov. 17, 2008, 6 pages.

*Hudson Surgical Design* v. *Zimmer Holdings, Inc., et al.,* Revised Final Claim Construction Chart, filed Mar. 11, 2009, 18 pages.

Haines et al., Accelerated Examination Search Statement and Support Document for Femoral Prosthetic Implant from U.S. Appl. No. 12/638,692, dated Dec. 15, 2009, 85 pages.

Office Action for U.S. Appl. No. 12/638,692, mailed Oct. 22, 2010, 19 pages.

Supplemental Information Disclosure Statement filed in U.S. Appl. No. 12/638,692, on Nov. 16, 2010, 19 pages.

Haines et al., Corrected Accelerated Examination Search Statement and Support Document for Femoral Prosthetic Implant from U.S. Appl. No. 12/757,778, dated Apr. 9, 2010, 104 pages.

Office Action for U.S. Appl. No. 11/933,298, mailed Dec. 2, 2010, 20 pages.

Freeman Samuelson, Total Knee Systems, Biomet, Inc., 1994, attached as Exhibit F, 60 pages.

Freeman, M.A.R., and Samuelson, K.M., Protek® Mark II Total Knee Replacement System, published 1985, 32 pages, attached as Exhibit G.

Protek F/S Modular Total Knee Replacement System, published by Protek, Jan. 1991, pp. 1-58, attached as Exhibit H.

Buechel, F.F. et al., "Low Contact Stress Meniscal Bearing Unicompartmental Knee Replacement: Long-Term Evaluation of Cemented and Cementless Results," Journal of Orthopaedic Rheumatology, presented at the 57th Annual American Academy of Orthopaedic Surgeons Meeting, New Orleans, LA, Feb. 11, 1990, Bates No. DEP00004096-DEP00004107, 13 pages.

N.J. Unicompartmental Knee, Sep. 15, 1989, Bates No. DEP00004108-DEP00004116, 10 pages.

Buechel, F.F., "NJ LCS Unicompartmental Knee System with Porocoat: Surgical Procedure," Oct. 24, 1994, Bates No. DEP00004117-DEP00004130, 15 pages.

Buechel, F.F., "NJ LCS Unicompartmental Knee System with Porocoat," 1994, Bates No. DEP00004142-DEP4152, 11 pages.

Engh, G.A. et al., "The AMK Total Knee System, Design Rationale and Surgical Procedure," Published by DePuy, 1989, Bates No. DEP00004153-DEP00004201, 50 pages.

Chapman, Michael W., ed., "Primary Total Knee Arthroplasty," Operative Orthopaedics, vol. 1, published by J.B. Lippincott Co., Philadelphia, 1988, pp. 719-725 and p. 86, Bates No. DEP00004236-DEP00004247.

Crossett, L.S. et al., "AMK Congruency Instrument System, Surgical Technique," published by DePuy, 1997, Bates No. DEP00004252-DEP00004267, 17 pages.

Engh, G.A. et al., "AMK Surgical Technique," published by DePuy, 1989, Bates No. DEP00004299-DEP00004329, 32 pages.

Desjardins, D. et al., "Interax Operative Techniques," Interax, 1994, Bates No. DEP00004391-DEP00004411, 22 pages.

Desjardins, D. et al., "Interax Total Knee Operative Technique," Interax, 1993, Bates No. DEP00004412-DEP00004432, 22 pages.

Baird et al., "LCS Uni: Unicompartmental Knee System with Porocoat," published by DePuy; 1991, Bates No. DEP00004452-DEP00004462, 12 pages.

Oxford Meniscal Knee Phase II Unicompartmental Replacement, published by Biomet prior to Jun. 7, 1994, Bates No. DEP00004509-DEP00004515, 8 pages.

Scott, R.D. et al., "P.F.C. Signa Uni-compartmental Knee System," published by Johnson & Johnson, 1998, Bates No. DEP00004531-DEP00004539, 10 pages.

Scott, R.D. et al., "Unicondylar Unicompartmental Replacement for Osteoarthritis of the Knee," Journal of Bone and Joint Surgery, vol. 63-A, No. 4, Apr. 1, 1981, pp. 536-544, Bates No. DEP00004764-DEP00004775.

Office Action for U.S. Appl. No. 12/757,778, mailed Nov. 15, 2010, 17 pages.

International Preliminary Report on Patentability, PCT/US2011/047414, Feb. 12, 2013, 7 pages.

International Search Report and Written Opinion, PCT/US2011/047414, Mar. 15, 2012, 12 pages.

\* cited by examiner

STRUCTURES FOR USE IN ORTHOPAEDIC IMPLANT FIXATION AND METHODS OF INSTALLATION ONTO A BONE

CROSS REFERENCE TO RELATED APPLICATIONS

The present application claims the benefit of U.S. Provisional Patent Application Ser. No. 60/372,902 filed on Aug. 12, 2010, the contents of which are hereby incorporated by reference in their entirety.

FIELD OF THE INVENTION

The present invention relates generally to orthopaedic implants, and more particularly relates to structures and mechanisms for anchoring, fastening, retaining, locking and/or fixation of components used in association with knee prostheses or other orthopaedic implants to bone, and methods for installing orthopaedic implants to bone.

BACKGROUND

Disease and trauma affecting one or more articular surfaces of the knee joint are commonly treated by surgically replacing the end portions of the femur and tibia bones with prosthetic femoral and tibial implant components, and in some cases replacing the patella with a patella implant component. Such surgical procedures are often referred to as total knee replacement (TKR). In TKR surgeries, a surgeon typically affixes a pair of articulating prosthetic components to the patient's femur and tibia bone structures; namely, a femoral implant component affixed to the inferior end portion of the patient's femur bone and a tibial component affixed to the superior end portion of the patient's tibia bone.

Certain knee prostheses, including the knee prostheses illustrated and described in U.S. Pat. No. 7,326,252 to Otto et al., the contents of which are incorporated herein by reference, include femoral implant components having flexed or backdrafted interior surfaces that facilitate locking of the femoral implant component onto a resected inferior end portion of the femur bone. Interior surfaces of the femoral implant component, such as anterior and posterior interior surfaces, may converge or taper towards one another in a superior-inferior direction. These types of backdrafted femoral implant components can be installed onto the femur bone by at least slightly rotating the femoral implant component during axially displacement onto the resected end portion of the femur bone. In this manner, the femoral implant component is said to be "rolled on" the end portion of the resected femur bone to accommodate for the particular configuration of the component and to capture the resected end portion of the femur bone within an interior region of the femoral implant component.

Conventional femoral implant components, which have interior anterior and posterior surfaces that are arranged generally parallel to one another or which are slightly divergent in a superior-to-inferior direction, can be installed or impacted in a straight line onto the resected end portion of the femur bone generally along the anatomic axis of the femur bone. These conventional femoral implant components may utilize pegs or posts to further secure the femoral implant component on the resected end portion of the femur bone via insertion of the pegs into prepared holes pre-cut into the resected end portion of the femur bone. However, the above-discussed "roll on" installation procedure to install femoral implant components having backdrafted surfaces onto a resected end portion of the femur bone can hinder if not entirely prevent the use of conventional pegs or posts that are designed to be impacted in a straight line since the pegs or posts risk opening up or damaging the prepared holes and/or causing interference with the prepared holes as the femoral implant component is rolled onto the resected end portion of the femur bone.

Thus, there remains a need for providing orthopaedic implants with improved structures and mechanisms for anchoring, fastening, retaining, locking and/or fixation of components used in association with knee prostheses or other orthopaedic implants to the resected end portion of a bone, and methods for installing the orthopaedic implant onto the resected end portion of the bone. The present invention satisfies this need and provides other benefits and advantages in a novel and unobvious manner.

SUMMARY

While the actual nature of the invention covered herein can only be determined with reference to the claims appended hereto, certain forms of the invention that are characteristic of the embodiments disclosed herein are described briefly as follows.

In one form of the invention, an orthopaedic implant is provided for installation onto an end portion of a bone. The implant includes a base portion and first and second transverse portions extending transversely from the base portion to thereby define an inner region of the implant sized for receipt of the end portion of the bone therein. The implant further includes at least one anchor structure projecting from the base portion and sized and configured for receipt within an opening formed in the end portion of the bone. The anchor structure extends along a longitudinal axis and includes a proximal end attached to the base portion and an opposite distal end, and the anchor structure further includes a tapered outer surface that inwardly tapers in a proximal-to-distal direction along the longitudinal axis.

In another form of the invention, an orthopaedic implant is provided for installation onto an end portion of a bone. The implant includes a base portion and at least one anchor structure projecting from the base portion and sized and configured for receipt within an opening formed in the end portion of the bone. The anchor structure extends along a longitudinal axis and includes a proximal end attached to the base portion and an opposite distal end, and the anchor structure further includes a tapered outer surface that inwardly tapers in a proximal-to-distal direction along the longitudinal axis. The anchor structure also includes one or more grooves extending into the tapered outer surface, and the implant further comprises a flowable material positioned about at least a portion of the tapered outer surface of the anchor structure and positioned within the grooves, with the flowable material configured to cure to a hardened state. In one embodiment, the grooves comprise a plurality of circumferential grooves extending about the tapered outer surface of the anchor structure. In another embodiment, the flowable material comprises a bone cement material or a bone paste material.

In another form of the invention, an orthopaedic implant is provided for installation onto an end portion of a bone. The implant includes a base portion and first and second transverse portions extending transversely from the base portion to thereby define an inner region of the implant sized for receipt of the end portion of the bone therein, with the first transverse portion defining a first bone interface surface that inwardly converges relative to a second bone interface surface defined by the second transverse portion in a direction extending away from the base portion. The implant further includes at least one anchor structure projecting from the base portion and sized and configured for receipt within an opening formed in the end portion of the bone. The anchor structure extends along a longitudinal axis and includes a proximal end attached to the base portion and an opposite distal end, and the anchor structure further includes a tapered outer surface defining a concave curvature extending generally along the longitudinal axis and inwardly tapering in a proximal-to-distal direction along said longitudinal axis.

In another form of the invention, a method for installing an orthopaedic implant onto an end portion of a bone includes providing an orthopaedic implant including a base portion, at least one anchor structure projecting from the base portion, and first and second transverse portions extending transversely from the base portion to thereby define an inner region of the implant sized for receipt of the end portion of the bone therein, with the anchor structure extending along a longitudinal axis and including a proximal end attached to the base portion and an opposite distal end, and the anchor structure including a tapered outer surface that inwardly tapers in a proximal-to-distal direction along the longitudinal axis. The method further includes generally aligning the inner region of the implant with the end portion of the bone, rolling the orthopaedic implant onto the end portion of the bone by displacing the implant generally along an anatomic longitudinal axis of the bone and rotating the implant generally about a pivot axis arranged transverse to the anatomic longitudinal axis of the bone, and inserting the anchor structure into an opening formed in the end portion of the bone during the rolling. In a further embodiment, the anchor structure includes one or more grooves extending into the tapered outer surface, and the method further comprises positioning a flowable material about at least a portion of the tapered outer surface of the anchor structure and within the grooves, and curing the flowable material to a hardened state. In one specific embodiment, the grooves comprise a plurality of circumferential grooves extending about the tapered outer surface of the anchor structure. In another specific embodiment, the flowable material comprises a bone cement material or a bone paste material.

It is one object of the present invention to provide orthopaedic implants with improved structures and mechanisms for anchoring fastening, retaining, locking and/or fixation of components used in association with knee prostheses or other orthopaedic implants to the end portion of a bone, and methods for installing the orthopaedic implant onto the end portion of the bone. Further embodiments, forms, features, aspects, benefits, objects, and advantages of the present application will become apparent from the detailed description and figures provided herewith.

DESCRIPTION OF THE ILLUSTRATED EMBODIMENTS

Figure 1:
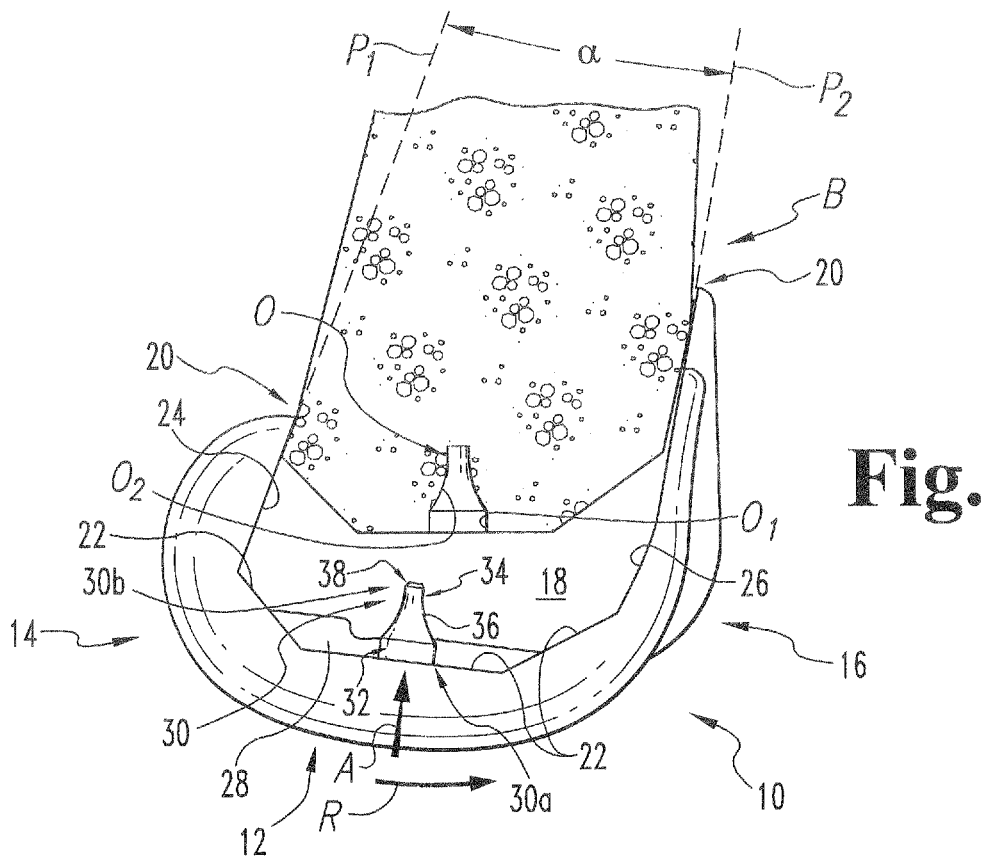
FIG. 1 is a side view of a femoral implant component having an anchor structure according to one form of the present invention, as shown with respect to a resected end portion of a femur bone.

For the purpose of promoting an understanding of the principles of the present invention, reference will now be made to the embodiments illustrated in the drawings and specific language will be used to describe the same. It will nevertheless be understood that no limitation of the scope of the invention is hereby intended. Any alterations and further modifications in the described embodiments, and any further applications of the principles of the invention as described herein are contemplated as would normally occur to one skilled in the art to which the invention relates.

Referring to FIG. 1, shown therein is one form of an orthopaedic implant 10 configured for implantation onto an end portion of a bone. In the illustrated embodiment, the orthopaedic implant 10 constitutes a femoral implant component 10 configured for implantation onto a resected inferior end portion of a femur bone B. However, as will be discussed below, other types and configurations of orthopaedic implants are also contemplated for implantation onto femur bones, tibia bones, or other bone structures.

Figure 5:
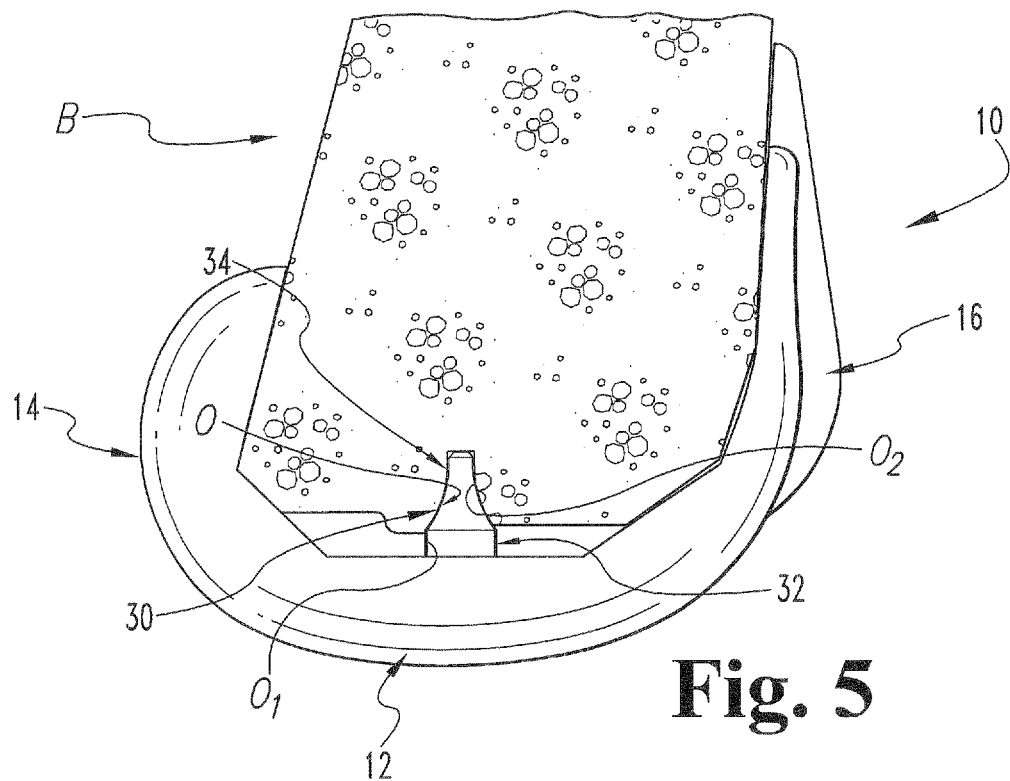
FIG. 5 is a side view of the femoral implant component illustrated in FIG. 1, as installed on the resected end portion of the femur bone.

In the illustrated embodiment, the femoral implant component 10 generally includes a base portion 12, a posterior transverse portion 14 extending transversely from a posterior end of the base portion 12, and an anterior transverse portion 16 extending transversely from an anterior end of the base portion 12 and arranged generally opposite the posterior transverse portion 14. The femoral implant component 10 includes an inner region 18 bound by the base portion 12 and the transverse portions 14, 16, and an opening 20 is defined between the distal ends of the posterior and anterior transverse portions 14, 16 which communicates with the inner region 18. The opening 20 is sized for receipt of the resected inferior end portion of the femur bone B therethrough for positioning of the resected inferior end portion within the inner region 18 of the femoral implant component 10 (FIG. 5).

The base portion 12 defines an inner bone interface surface or surfaces 22, the posterior transverse portion 14 defines an inner bone interface surface 24 extending along a first plane $P_1$, and the anterior transverse portion 16 defines an inner bone interface surface 26 extending along a second plane $P_2$. The plane $P_1$ extending along the bone interface surface 24 is tapered relative to the plane $P_2$ extending along the bone interface surface 26 at a taper angle α. More specifically, the plane $P_1$ of the bone interface surface 24 inwardly converges relative to the plane $P_2$ of the bone interface surface 26 at a taper angle α in a direction extending away from the base portion 12 (i.e., in an inferior-to-superior direction). In this manner, the femoral implant component 10 is said to have flexed or backdrafted bone interface surfaces that inwardly converge towards one another as the posterior and anterior transverse portions 14, 16 extend from an inferior aspect of the femoral implant component 10 (i.e., from the base portion 12) towards a superior aspect of the femoral implant component 10 (i.e., toward the distal ends of the posterior and anterior transverse portions 14, 16). In the illustrated embodiment, the bone interface surfaces 22, 24 and 26 are substantially flat and planar. However, in other embodiments, the bone interface surfaces 22, 24 and 26 may be curved, partially curved, or curvilinear. Additionally, the bone interface surfaces 22, 24 and 26 may be provided with surface features that further facilitate engagement with bone and/or which facilitate bony fusion with adjacent bone tissue. Such surface features include, for example, grooves, pores, ribs, teeth, spikes, knurling, surface roughening, or other suitable bone engagement features. For example, in the illustrated embodiment, the femoral implant component 10 optionally includes at least one rib 28 extending along the bone interface surface 22 of the base portion 12 to further facilitate engagement with bone.

The femoral implant component 10 includes at least one fastener or anchor structure 30 projecting axially from the bone interface surface 22 of the base portion 12 and into the inner region 18. In the illustrated embodiment, the anchor structure 30 is generally centrally located along the bone interface surface 22. However, other positions and locations of the anchor structure 30 are also contemplated. The anchor structures 30 are sized and shaped for receipt within openings O formed in the resected end portion of the femur bone B. Each of the anchor structures 30 has an overall length l extending generally along a longitudinal axis L and includes a proximal end 30a attached to the base portion 12 and an opposite distal end 30b. In the illustrated embodiment, the anchor structure 30 generally includes a mount portion 32 projecting from the bone interface surface 22 of the base portion 12, and a tapered portion 34 extending axially from the mount portion 32, further details of which will be set forth below.

As the femoral implant component 10 is installed or rolled onto the resected end portion of the femur bone B, the anchor structures 30 are sized and shaped for receipt within corresponding openings O formed in the femur bone B without gouging into or otherwise traumatizing or damaging the bone tissue adjacent the openings O. In the illustrated embodiment, the openings O in the femur bone B each include a first portion $O_1$ having a size and shape corresponding to the size and shape of the mount portion 32 of the anchor structure 30, and a second portion $O_2$ having a size and shape corresponding to the size and shape of the tapered portion 34 of the anchor structure 30. Although the openings O have been illustrated and described as having a particular shape and configuration, openings having other shapes and configurations are also contemplated.

In one embodiment, the openings O may be pre-formed in the resected end portion of the femur bone B via one or more drills, punches, or other suitable cutting tools. However, in other embodiments, the openings O may be formed via pressing the anchor structures 30 into bone tissue as the femoral implant component 10 is rolled onto the resected end portion of the femur bone B. In other words, instead of pre-forming the openings O in bone tissue to receive the anchor structures 30, the openings O may be formed during installation of the femoral component 10 by pressing the anchor structures 30 into bone tissue. Notably, forming the openings O via pressing the anchor structures 30 into the bone tissue will provide the openings O with a size and shape that closely corresponding to the size and shape of the anchor structures 30. In other words, forming the openings O via pressing the anchor structures 30 into the bone tissue will not create an oversized opening having excess clearance between the bone tissue and the anchor structures 30.

Figure 2:
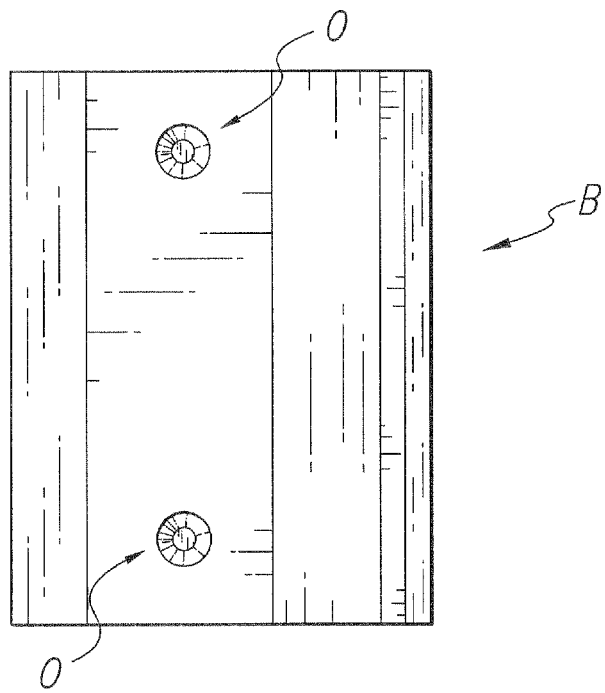
FIG. 2 is top plan view of the resected end portion of the femur bone illustrated in FIG. 1.

In the illustrated embodiment, the femoral implant component 10 includes two anchor structures 30 projecting from the base portion 12 which are sized and shaped for receipt within a corresponding pair of openings O (FIG. 2) formed in the resected end portion of the femur bone B. However, it should be understood that the femoral implant component 10 may be provided with any number of the anchor structures 30, including a single anchor structure or three or more anchor structures. Additionally, although the anchor structures 30 are illustrated as projecting from the base portion 12, it should be understood that the anchor structures 30 may project from either of the posterior and anterior transverse portions 14, 16.

Figure 3:
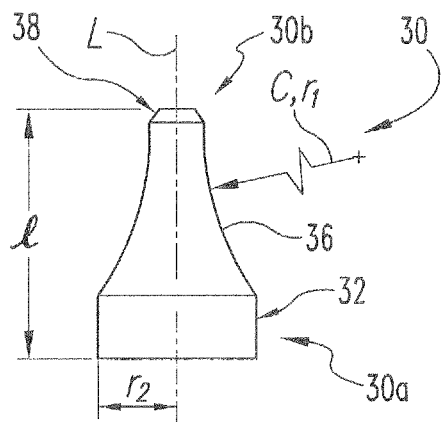
FIG. 3 is an enlarged side view of the anchor structure illustrated in FIG. 1.

Referring collectively to FIGS. 1 and 3, in the illustrated embodiment, the mount portion 32 is generally cylindrical in shape. However, in other embodiments, the mount portion 32 may take on other shapes and configurations including, for example, a hexagonal configuration, a rectangular configuration, or other suitable shapes and configurations. In still other embodiments, the mount portion 32 may be eliminated such that the tapered portion 34 projects directly from the base portion 12 of the femoral implant component 10. In one embodiment, the anchor structures 30 are formed integral with the base portion 12 (or the transverse portions 14, 16) to define a unitary, single-piece, monolithic implant structure. However, in other embodiments, the anchor structures 30 may be formed separately from the remainder of the femoral implant component 10 and attached to the base portion 12 (or the transverse portions 14, 16) by various attachment methods including, for example, welding, bonding, threading, fastening, pinning, or by any other suitable attachment method.

In the illustrated embodiment, the tapered portion 34 includes a tapered outer surface 36 that inwardly tapers in a proximal-to-distal direction along the longitudinal axis L, and a chamfered or beveled distal end surface 38 extending from the tapered outer surface 36 to the distal-most end of the anchor structure 30. In one embodiment, the tapered surface 36 extends along at least one-half of the overall length l of the anchor structure 30. In another embodiment, the tapered surface 36 extends along at least two-thirds of the overall length l of the anchor structure 30. In a further embodiment, the tapered surface 36 tapers substantially entirely along the length of the tapered portion 34 from the mount portion 32 to the chamfered end surface 38. However, it should be understood that in other embodiment, the tapered surface 36 may extend along other lengths of the anchor structure 30 and may be tapered along other lengths of the tapered portion 34.

In the illustrated embodiment, the tapered surface 36 has a generally conical shape to thereby provide the taper portion 34 with a conical configuration. More specifically, the tapered surface 36 has a generally frustoconical shape to thereby provide the tapered portion 34 with a frustoconical configuration. However, it should be understood that the tapered surface 36 may be provided with other suitable shapes and configurations. Moreover, in the illustrated embodiment, the tapered surface 36 defines a concave curvature C extending in a proximal-to-distal direction along the longitudinal axis L. Additionally, in the illustrated embodiment, the concave curvature C defines a varying taper angle and taper rate relative to the longitudinal axis L that decreases in a proximal-to-distal direction along the longitudinal axis L. In other words, the concave curvature C defines a steeper taper angle and tapers at a greater rate along the proximal portion of the tapered surface 36 compared to the distal portion of the tapered surface 36. In some embodiments, the concave curvature C may extend along an arc having a constant or uniform radius of curvature. However, in other embodiments, the concave curvature C may extend along an arc having a varying radius of curvature.

In a further embodiment, the concave curvature C extends along a concave surface radius $r_1$ that is larger than a maximum convex surface radius $r_2$ of the anchor structure 30 measured from the longitudinal axis L. In some embodiments, the concave surface radius $r_1$ of the tapered surface 36 falls within a range of approximately 0.200 inches to 0.500 inches, and in some instances is approximately 0.350 inches. In other embodiments, the maximum convex surface radius $r_2$ of the tapered surface 36 (and the cylindrical base 32) is approximately 0.282 inches. However, it should be understood that these sizes are exemplary and that other sizes are also contemplated. Additionally, although the taper surface 34 has been illustrated and described as having a particular shape and configuration, it should be understood that other shapes and configurations are also contemplated, including configurations where the tapered outer surface 36 defines a linear taper angle and/or multiple taper angles, or where the tapered outer surface 36 defines a curvilinear configuration.

In the illustrated embodiment, the anchor structure 30 is generally configured as a lug extending axially from the base portion 12 of the femoral implant component 10. However, in other embodiments, the anchor structure 30 may be configured as a pin, a peg, a post, a fin, a flute, or any other mechanical anchor or fastener structure configured to secure the femoral implant component 10 to the resected distal portion of the femur bone B. Additionally, it should be understood that the shape and configuration of the anchor structure 30 is not limited to that shown in the drawing figures, but may take on other shapes and configurations depending on the type and size of the implant with which the anchor structure is to be used and the path along which the implant is displaced during installation onto the resected distal portion of the femur bone B. The curvature of the tapered surface 36 can be determined by a variety of factors, including factors relating to the angle of misalignment between the anchor structure 30 and the opening O in the bone B within which the anchor structure 30 is positioned. Some of these factors include, but are not limited to, the geometry of the implant (including the implant's size, shape and configuration), the shape and/or diameter of the mounting portion 32 of the anchor structure 30, the smallest diameter of the anchor structure 30, the height of the anchor structure 30, and/or other geometric aspects of the anchor structure 30.

Figure 4:
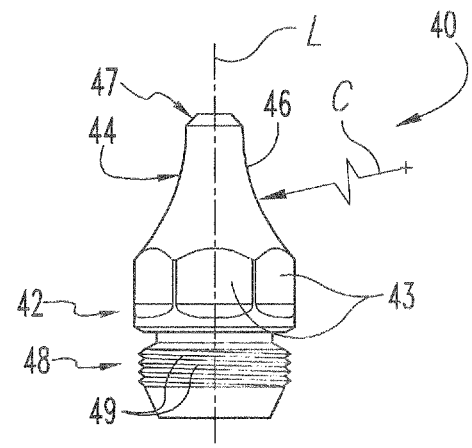
FIG. 4 is an enlarged side view of an anchor structure according to another embodiment of the present invention.

Referring to FIG. 4, shown therein is another embodiment of an anchor structure 40 suitable for use in association with the femoral implant component 10 or other implant components. The anchor structure 40 is configured similar to the anchor structure 30 illustrated and described above, including a mounting portion 42 and a tapered portion 44 defining a tapered outer surface 46 configured similar to the tapered outer surface 36 of the anchor structure 30. Additionally, the tapered outer surface 46 similarly defines a concave curvature C extending in a proximal-to-distal direction along the longitudinal axis L and a chamfered distal end surface 47 extending from the tapered surface 46 to the distal-most end of the anchor structure 40. However, unlike the cylindrical-shaped mount portion 32 of the anchor structure 32, the base portion 42 has a hexagonal configuration defining a hexagonal-shaped outer surface having a series of flattened surfaces 43 configured for engagement with a rotational driving tool such as a wrench (not shown). Additionally, unlike the anchor structures 30, the anchor structure 40 includes a threaded stem 48 extending axially from the base portion 42 and defining external threads 49 configured from threading engagement with internal threads formed in a corresponding threaded opening in the base portion 12 or the transverse portion 14, 16 of the femoral implant component 10 to securely attach the anchor structure 40 to the femoral implant component 10.

Figures 6A, 6B, 6C, 6D, 6E, 6F, 6G, 6H:
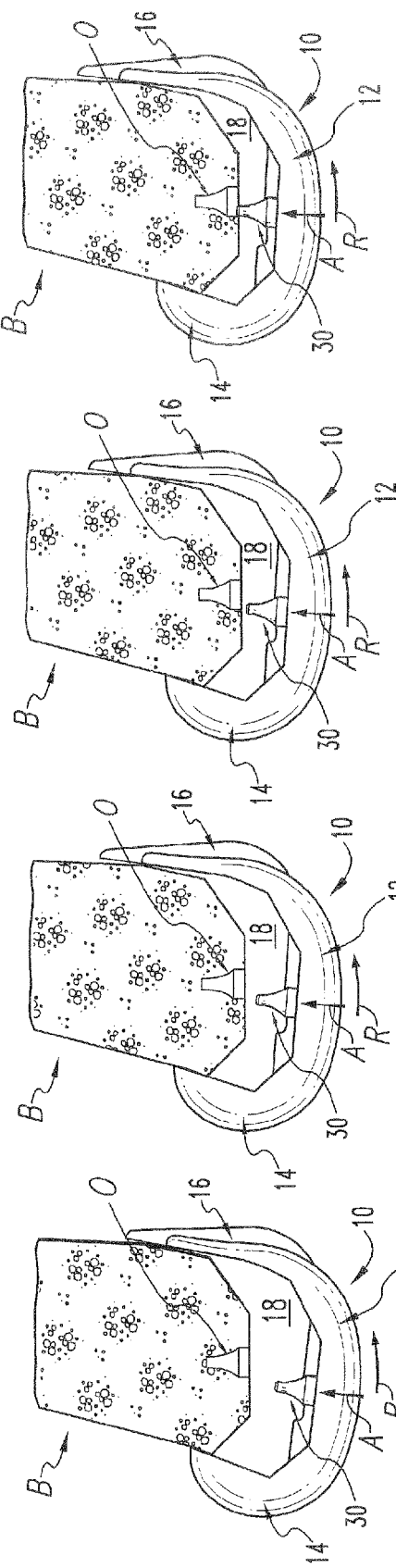
FIGS. 6A-6H are a series of side views of the femoral implant component illustrated in FIG. 1 during installation onto the resected end portion of the femur bone as the femoral implant component is rotated and translated with respect to the resected end portion of the femur bone.

Referring to FIGS. 6A-6H, shown therein is a series of side views of the femoral implant component 10 during installation onto the resected end portion of the femur bone B. As shown in FIG. 6A, the inner region 18 of the femoral implant component 10 is initially generally aligned with the resected end portion of the femur bone B. As shown in FIGS. 6B-6G, the femoral implant component 10 is then rolled onto the resected end portion of the femur bone B by axially displacing the femoral implant component 10 generally along the anatomic longitudinal axis of the femur bone B in the direction of arrow A while slightly rotating the femoral implant component 10 generally about a pivot/hinge axis arranged transverse to the anatomic longitudinal axis of the femur bone B in the direction of arrow R. Additionally, as the femoral implant component 10 is translated and rotated (i.e., rolled) with respect to the resected end portion of the femur bone B, the anchor structures 30 are gradually inserted into the openings O formed in the resected end portion of the femur bone B. As shown in FIGS. 5 and 6H, when the femoral implant component 10 is fully installed onto the resected end portion of the femur bone B, the anchor structures 30 are fully inserted into the openings O.

As should be appreciated, rotating the femoral component 10 onto the resected end portion of the femur bone B in the direction of arrow R as the femoral implant component 10 is axially translated in the direction of arrow A allows the backdrafted inner surfaces 24, 26 defined by the posterior and anterior transverse portions 14, 16 of the femoral implant component 10 to physically clear the resected bone during installation onto the femur bone B. Notably, if the femoral implant component 10 were simply impacted in a straight line onto the resected end portion of the femur bone B, as is typically the case with femoral implant components having anterior and posterior inner surfaces that are arranged generally parallel or slightly divergent with respect to one another, the backdrafted inner surfaces would not physically clear the resected end portion of the femur bone B, thereby interfering with or preventing installation of the femoral component onto the femur bone B.

As indicated above, the anchor structure 30 is sized and configured for receipt within the opening O formed in the resected end portion of the femur bone B during installation of the femoral component 10 onto the femur bone B. Since the tapered portion 34 of the anchor structure 30 has a relatively smaller radial profile adjacent the distal end 30b relative to the proximal end 30a, the anchor structure 30 may be gradually inserted into the opening O without gouging into or otherwise traumatizing or damaging the bone tissue adjacent the opening O. Moreover, movement of the tapered portion 34 along the first opening portion $O_1$ toward the second opening portion $O_2$ as the femoral implant component 10 is installed onto the resected end portion of the femur bone B helps facilitate rolling of the femoral implant component 10 onto the femur bone B. In this manner, the first opening portion $O_1$ serves as a pathway for receipt of the tapered portion 34 of the anchor structure 30 as the femoral component 10 is rolled onto the femur bone B to avoid interference between the tapered portion 34 and the adjacent bone tissue. Specifically, as the femoral implant component 10 is rolled onto the resected end portion of the femur bone B, the tapered portion 34 of the anchor structure 30 has room to shift within the first opening portion $O_1$ without interfering with the edges surrounding the first opening portion $O_1$ which might otherwise break off or gouge into the adjacent bone tissue and cause the first opening portion $O_1$ to widen, thereby resulting in conservation of the bone tissue surrounding the first opening portion $O_1$. As indicated above, in one embodiment, the openings O may be pre-formed in the resected end portion of the femur bone B for receipt of the anchor structures 30. However, in other embodiments, the openings O may be formed via pressing the anchor structures 30 into bone tissue as the femoral implant component 10 is rolled onto the resected end portion of the femur bone B.

As should be appreciated, maintaining the bone tissue surrounding the first opening portion $O_1$ may result in more secure engagement of the mount portion 32 of the anchor structure 30 within the first opening portion $O_1$ when the femoral component is fully installed onto the resected end portion of the femur bone B. As illustrated in FIG. 5, once the femoral implant component 10 is in its final position on the resected end portion of the femur bone B, the tapered portion 34 of the anchor structure 30 is positioned securely within the second opening portion $O_2$ of the opening O, and the mount portion 32 of the anchor structure 30 is positioned securely within the first opening portion $O_1$. Because the size and shape of the anchor structure 30 and the opening O in the bone B closely correspond to one another (both of which are relatively smaller than traditional pegs and prepared bone openings used in connection with standard femoral implant components), the anchor structure 30 has a relatively tighter fit within the opening O in which it is received, and the femoral implant 10 is therefore more tightly secured onto the resected end portion of the femur bone B.

Figure 7:
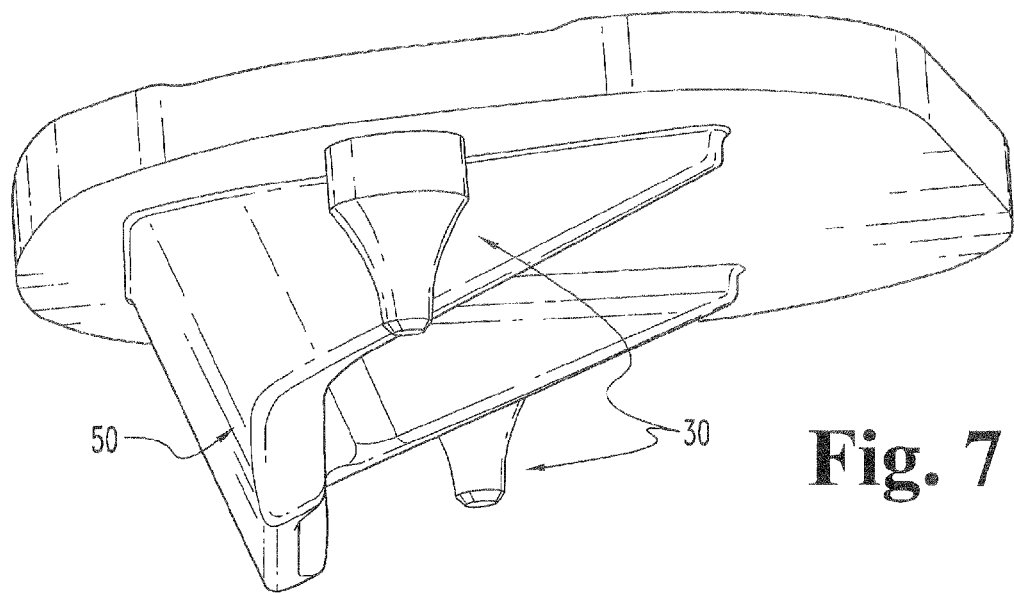
FIG. 7 is a side perspective view of a tibial baseplate having an anchor structure according to one form of the present invention.
Figure 8:
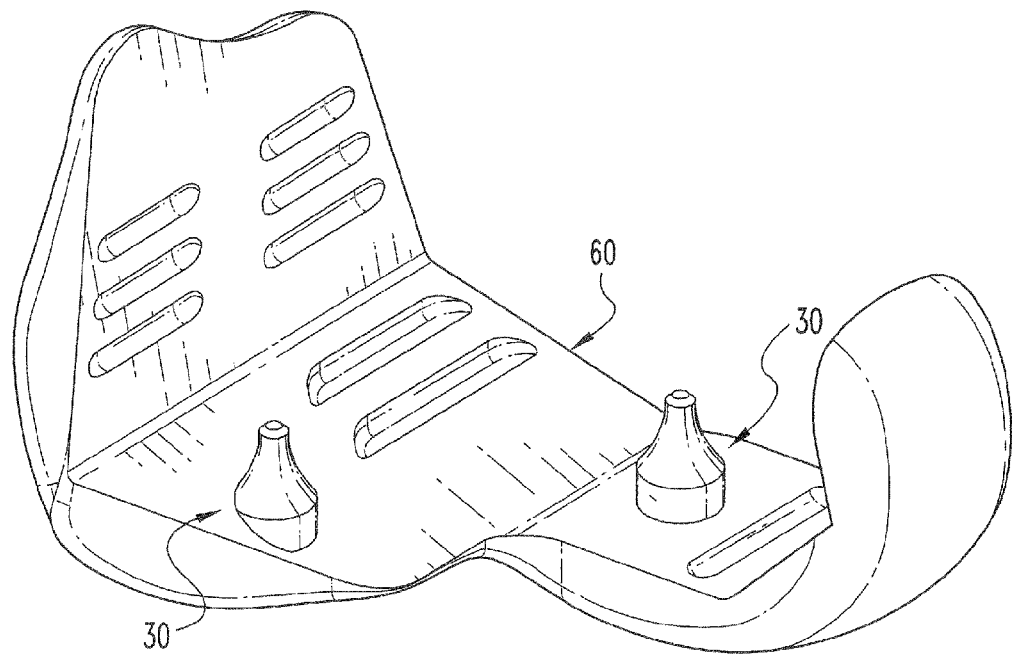
FIG. 8 is a side perspective view of a bi-compartmental femoral implant component having an anchor structure according to one form of the present invention.
Figure 9:
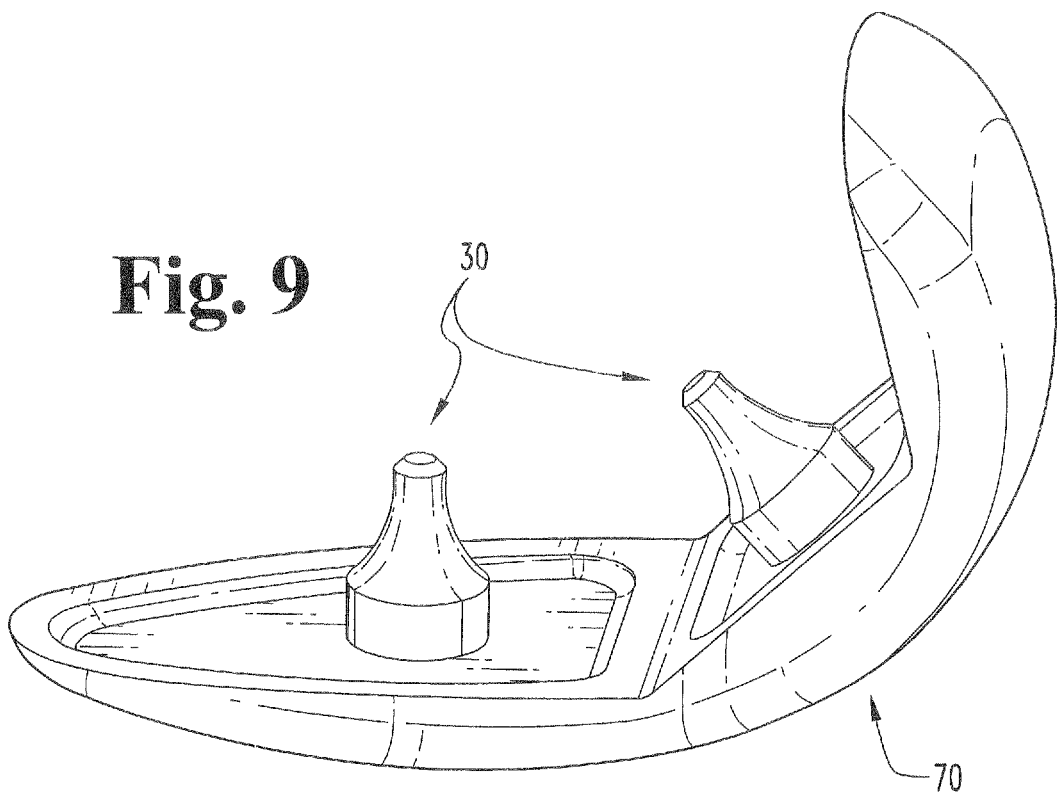
FIG. 9 is a side perspective view of a unicondylar femoral implant component having an anchor structure according to one form of the present invention.

It should be understood that use of the anchor structure 30 is not limited to use with the femoral component 10 illustrated and described above, but can also be used in association with a wide variety of orthopaedic implant components including, for example, the tibial baseplate implant component 50 illustrated in FIG. 7, the hi-compartmental femoral implant component 60 illustrated in FIG. 8, the unicondylar femoral implant component 70 illustrated in FIG. 9, segmental implant components (not shown), patellofemoral implant components (not shown), and any other orthopaedic implant component for which it may be desirable to "roll-on" the implant component instead of impacting the implant component in a generally straight line onto a resected distal portion of a bone, including implant components where fastening or anchor structures may be helpful in the installation and/or fixation/anchoring of the implant component onto an end portion of a bone.

Referring now to FIGS. 10-13, shown therein is a femoral implant component 100 according to another form of the present invention. As will be discussed more fully below, the femoral implant component 100 is configured similar to the femoral implant component 10 illustrated and described above except for the particular configuration of the anchor structures 130. In the illustrated embodiment, the anchor structure 130 are configured for use in association with a flowable material 150 (FIGS. 12 and 13) that is configured to cure or set to a non-flowable hardened state to further secure the anchor structures 130 within openings O' in the femur bone B, further details of which will be set forth below.

Figure 10:
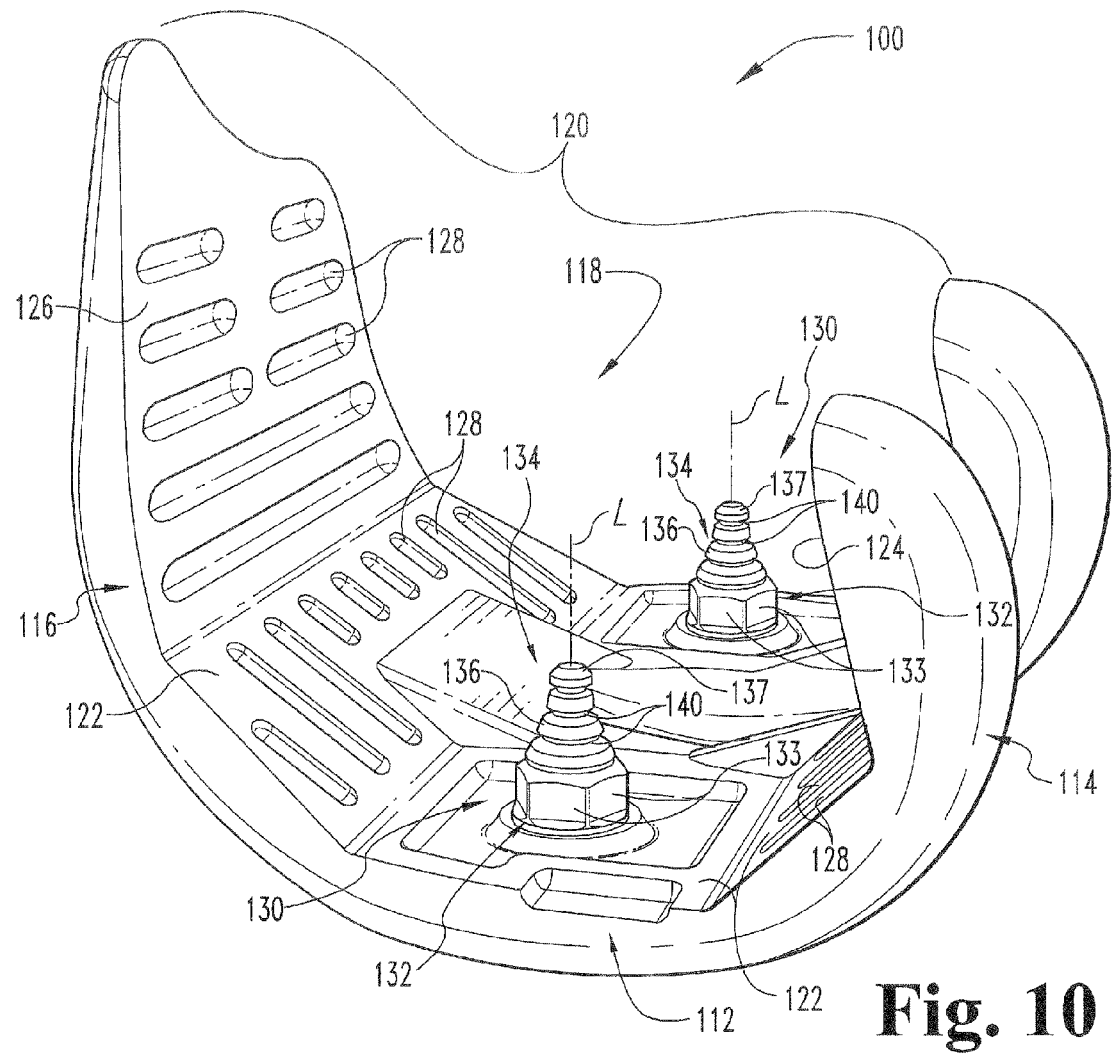
FIG. 10 is a side perspective view of a femoral implant component having an anchor structure according to another form of the present invention.
Figure 12:
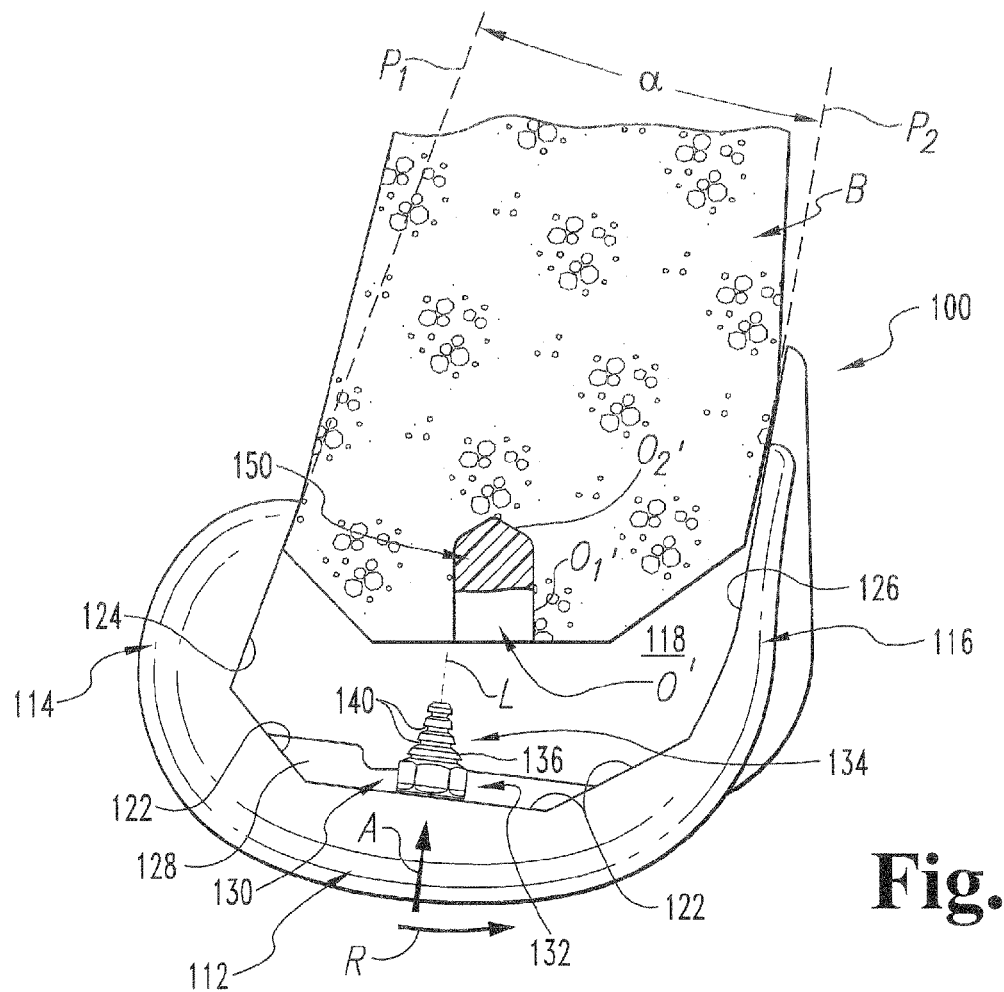
FIG. 12 is a side view of the femoral implant component illustrated in FIG. 10, as shown with respect to a resected end portion of a femur bone.
Figure 13:
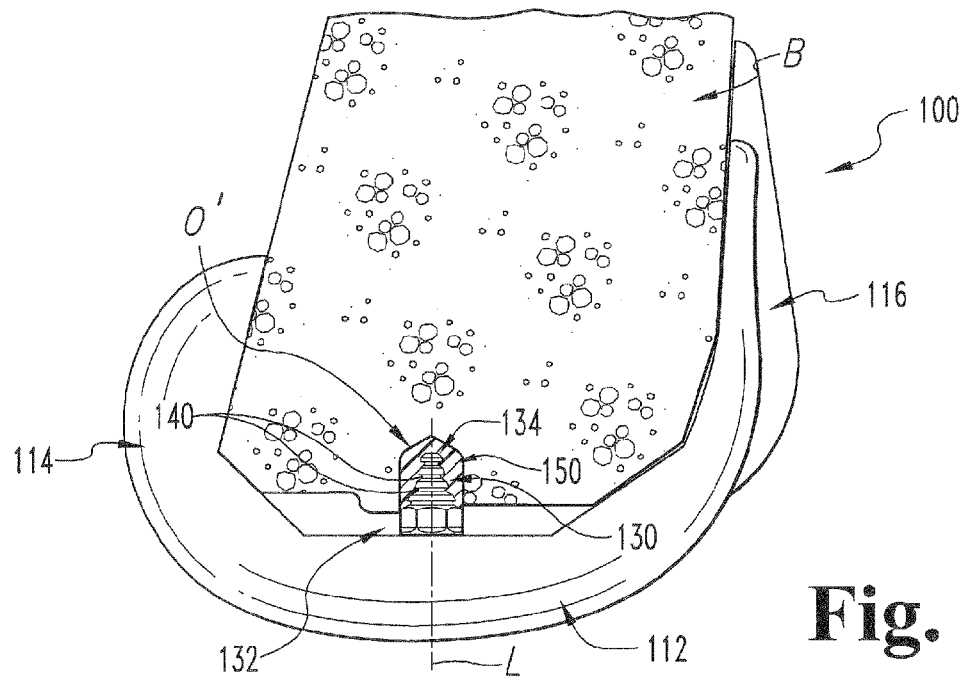
FIG. 13 is a side view of the femoral implant component illustrated in FIG. 10, as installed on the resected end portion of the femur bone.

Referring specifically to FIG. 10, the femoral implant component 100 is configured similar to the femoral implant component 10 illustrated and described above, except for the particular configuration of the anchor structures. Like the femoral implant component 10, the femoral implant component 100 generally includes a base portion 112, a posterior transverse portion 114 extending transversely from a posterior end of the base portion 112, and an anterior transverse portion 116 extending transversely from an anterior end of the base portion 112 and arranged generally opposite the posterior transverse portion 114. The femoral implant component 100 includes an inner region 118 bound by the base portion 112 and the transverse portions 114, 116, and an opening 120 is defined between the distal ends of the posterior and anterior transverse portions 114, 116 which communicates with the inner region 118. The opening 120 is sized for receipt of the resected inferior end portion of the femur bone B therethrough for positioning of the resected inferior end portion within the inner region 118 of the femoral implant component 100 (FIGS. 12 and 13).

The base portion 112 defines an inner bone interface surface or surfaces 122, the posterior transverse portion 114 defines an inner bone interface surface 124, and the anterior transverse portion 116 defines an inner bone interface surface 126. The bone interface surface 124 inwardly converges or tapers relative to the bone interface surface 126 in a direction extending away from the base portion 112 (i.e., in an inferior-to-superior direction). In this manner, the femoral implant component 100 is said to have flexed or backdrafted bone interface surfaces that converge towards one another as the posterior and anterior transverse portions 114, 116 extend from an inferior aspect of the femoral implant component 100 (i.e., the base portion 112) towards a superior aspect of the femoral implant component 100 (i.e., the distal ends of the posterior and anterior transverse portions 114, 116). In the illustrated embodiment, the bone interface surfaces 122, 124 and 126 are substantially flat and planar. However, in other embodiments, the bone interface surfaces 122, 124 and 126 may be curved, partially curved, or curvilinear.

Additionally, the bone interface surfaces 122, 124 and 126 may be provided with a series of grooves or channels 128 to facilitate engagement with bone and/or fusion of the implant component with adjacent bone tissue. If bone cement is used to further anchor the femoral component 100 to the resected end portion of the femur bone B, the bone cement may be dispersed within the grooves 128. As should be appreciated, some of the grooves 128 may be oriented in an anterior-posterior orientation for the control of cement hardening so as to increase stability of the femoral implant component 10 in a medial-lateral direction, whereas some of the grooves 128 may be oriented in a medial-lateral orientation for the control of cement hardening so as to increase shear resistance in an inferior-superior direction and/or to inhibit the femoral implant component 10 from rolling off of the femur bone B. In other embodiments, the bone interface surfaces 122, 124 and 126 may be provided with other surface features that further facilitate engagement with bone and/or bone fusion including, for example, pores, ribs, teeth, spikes, knurling, surface roughening, or other suitable bone engagement features.

Figure 11:
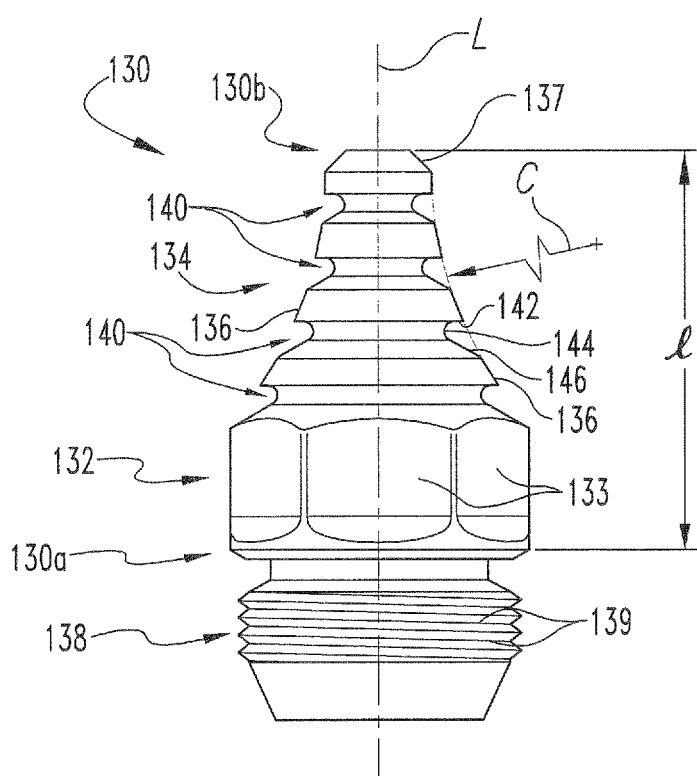
FIG. 11 is an enlarged side view of the anchor structure illustrated in FIG. 10.

Referring collectively to FIGS. 10 and 11, the femoral implant component 100 includes at least one fastener or anchor structure 130 projecting axially from the inner bone interface surface 122 of the base portion 112 and into the inner region 118. In the illustrated embodiment, the anchor structure 130 is generally centrally located along the bone interface surface 122. However, other positions and locations of the anchor structure 130 are also contemplated. The anchor structures 130 are sized and shaped for receipt within openings O' formed in the resected end portion of the femur bone B (FIGS. 12 and 13). Each of the anchor structures 130 has an overall length l extending generally along a longitudinal axis L and includes a proximal end 130a attached to the base portion 112 and an opposite distal end 130b. In the illustrated embodiment, the anchor structure 130 generally includes a mount portion 132 projecting from the inner bone interface surface 122 of the base portion 112, a tapered portion 134 extending axially from the mount portion 132 and defining a tapered outer surface 136, and a connection stem 138 extending axially from the mount portion 132 opposite the tapered portion 134 and configured for engagement with the base portion 112 of the femoral component 100.

In the illustrated embodiment, the mount portion 132 has a hexagonal configuration defining a hexagonal-shaped outer surface having a series of flattened surfaces 133 configured for engagement with a rotational driving tool such as a wrench (not shown). However, in other embodiments, the mount portion 132 may take on other configurations such as, for example, a cylindrical configuration, a rectangular configuration, or other suitable shapes and configurations. In still other embodiments, the mount portion 132 may be eliminated such that the tapered portion 134 projects directly from the base portion 112 of the femoral implant component 100. In the illustrated embodiment, the connection stem 138 is threaded so as to define external threads 139 configured from threading engagement with internal threads formed in a corresponding threaded opening (not shown) in the base portion 112 (or the transverse portion 114, 116) of the femoral implant component 100 to securely attach the anchor structure 130 to the femoral implant component 100. However, other shapes and configurations of the connection stem 138 are also contemplated. Additionally, in other embodiments, the anchor structures 130 may be formed integral with the base portion 112 (or the transverse portions 114, 116) to thereby define a unitary, single-piece, monolithic implant structure. In still other embodiments, the anchor structures 130 may be attached to the base portion 112 (or the transverse portions 114, 116) by various attachment methods including, for example, welding, bonding, fastening, pinning, or by any other suitable attachment method.

In the illustrated embodiment, the tapered portion 134 includes a tapered outer surface 136 defining a concave curvature C extending in a proximal-to-distal direction along the longitudinal axis L and which inwardly tapers in a proximal-to-distal direction along the longitudinal axis L, and a chamfered or beveled distal end surface 137 extending from the tapered outer surface 136 to the distal-most end of the anchor structure 130. In one embodiment, the tapered outer surface 136 is configured similar to the tapered outer surface 36 of the anchor structure 30. Accordingly, it should be understood that the features and aspects described above with regard to the tapered outer surface 36 of the anchor structure 30 also apply to the tapered outer surface 136 of the anchor structure 130. However, unlike the substantially smooth and uninterrupted tapered outer surface 36 of the anchor structure 30, the tapered outer surface 136 of the anchor structure 130 is provided with a series of circumferential grooves 140 extending about the longitudinal axis L. As will be discussed in further detail below, the circumferential grooves 140 are configured for receipt of a flowable material 150 which cures or sets to a non-flowable hardened state to further secure the anchor structures 130 within the bone tissue and to prevent the anchor structures 130 from pulling out of the cured/hardened material 150.

In the illustrated embodiment, the circumferential grooves 140 each have a generally planar undercut portion 142, a rounded or curved portion 144, and a planar angled portion 146 that cooperate with one another to provide the circumferential grooves 140 with an arcuate or how-shaped configuration. The generally planar undercut portion 142 extends from the tapered outer surface 136 and is arranged generally perpendicular or normal to the longitudinal axis L of the anchor structure 130. The rounded or curved portion 144 extends from the planar portion 142 and extends generally along a uniform radius of curvature. The planar angled portion 146 extends from the curved portion 144 and is obliquely angled relative to the longitudinal axis L. In one embodiment, the planar angled portion 146 is tapered at approximately a 45 degree angle relative to the longitudinal axis L. Although the circumferential grooves 140 are illustrated and described as having a particular shape and configuration, it should be understood that other shapes and configurations are also contemplated. For example, the grooves 140 may alternatively be configured as a single helical groove extending about the longitudinal axis L of the anchor structure 130, or may alternatively be configured to extend in other directions, including axially along the longitudinal axis L. Also, instead of having an arcuate bow-shaped configuration, the grooves 140 may alternatively be provided with a semi-circular configuration, a triangular configuration, a curvi-linear configuration, or any other suitable configuration. Additionally, although the illustrated embodiment of the anchor structure 130 includes four of the circumferential grooves 140, it should be understood that the anchor structure 130 may be provided with any number of grooves, including a single groove, two groove, three grooves, or five or more grooves.

Referring to FIGS. 12 and 13, like the femoral implant component 10 illustrated and described above, the femoral implant component 100 is installed or rolled onto the resected end portion of the femur bone B via axial displacement generally along the anatomic longitudinal axis of the femur bone B in the direction of arrow A while slightly rotating the femoral implant component 100 generally about a pivot/hinge axis arranged transverse to the anatomic longitudinal axis of the femur bone B in the direction of arrow R. Additionally, as the femoral implant component 100 is translated and rotated (i.e., rolled) with respect to the resected end portion of the femur bone B, the anchor structures 130 are gradually inserted into the openings O' formed in the resected end portion of the femur bone B.

Each of the anchor structures 130 are sized and shaped for receipt within corresponding openings O' during installation onto the resected end portion of the femur bone B without gouging into or otherwise traumatizing or damaging the bone tissue adjacent the openings O'. In the illustrated embodiment, each of the openings O' formed in the femur bone B includes a cylindrical-shaped portion $O_1'$ extending axially from the exterior surface of the femur bone B and having a diameter slightly larger than the distance between an opposite pair of the flattened surfaces 133 of the hexagonal-shaped mount portion 132 of the anchor structure 130, and a conical-shaped end portion $O_2'$ that generally tapers to a point. The openings O' may be pre-formed in the resected end portion of the femur bone B via one or more drills, punches, or other suitable cutting tools.

In one embodiment, the femoral implant component 100 includes two anchor structures 130 projecting from the base portion 112 and which are sized and shaped for receipt within a corresponding pair of openings O' formed in the resected end portion of the femur bone B. However, it should be understood that the femoral implant component 100 may be provided with any number of the anchor structures 130, including a single anchor structure or three or more anchor structure. Additionally, although the anchor structures 130 are illustrated as projecting from the base portion 112, it should be understood that the anchor structures 130 may project from either of the posterior and anterior transverse portions 114, 116. It should also be understood that although the openings O' have been illustrated and described as having a particular shape and configuration, openings having other shapes and configurations are also contemplated. As illustrated in FIGS. 12 and 13, in one embodiment, prior to installation of the femoral component onto the resected end portion of the femur bone B, each of the openings O' is partially filed with a flowable material 150 which cures or sets to a non-flowable hardened state. In a specific embodiment, the flowable material 150 comprises bone cement or bone paste, the purpose of which will be discussed below.

As shown in FIG. 13, when the femoral implant component 100 is installed onto the resected end portion of the femur bone B, the anchor structures 130 are fully inserted into the openings O'. As indicated above, prior to installation of the femoral component 100 onto the resected end portion of the femur bone B, each of the openings O' is partially filed with bone cement 150 or another hardenable/curable material. As the anchor structures 130 are inserted into the openings O', the bone cement 150 flows about the tapered portions 134 of the bone anchors 130 and into the circumferential grooves 140 so as to fully surround the tapered portions 134. Additionally, the bone cement 150 may also flow about and at least partially surround the base portions 132 of the bone anchors 130. After a period of time, the bone cement 150 cures and hardens about the tapered portion 134 and the mount portion 132, thereby providing a cylindrical-shaped lug having a shape similar to that of a conventional cylindrical-shaped lug used in association with traditional orthopaedic implant structures. As should be appreciated, the hardened bone cement 150 further secures the anchor structures 130 within the openings O' formed in the bone B, thereby further securing the femoral implant component 100 to the femur bone B and inhibiting removal of the femoral component 100 from the femur bone B. Additionally, the bone cement positioned within the circumferential grooves 140 prevents or otherwise inhibits the anchor structures 130 from pulling out of the cured/hardened bone cement 150. Specifically, the undercut portions 142 of the circumferential grooves 140 provides a shoulder or ledge which bears against the bone cement 150 to prevent or otherwise inhibit the anchor structures 130 from pulling out of the cured/hardened bone cement 150.

In the illustrated embodiment, prior to installation of the femoral component 100 onto the resected end portion of the femur bone B, each of the openings O' is partially filled with the bone cement 150. However, in other embodiments, the bone cement 150 may be injected into the open regions about the anchor structures 130 after the anchor structures 130 are inserted into the openings O'. For example, in an alternative embodiment, the anchor structures 130 may be provided with an axial opening (not shown) and one or more transverse openings (not shown) communicating between the axial opening and the outer surface 136 of the tapered portion and/or the circumferential grooves 140. A bone cement delivery device (not shown) may be positioned in communication with the axial opening, and the bone cement 150 may be injected into the axial opening, out the transverse openings, and into the open regions between the sidewalls of the openings O' and the anchor structures 130. Other suitable methods for injecting the bone cement 150 into the open regions between the sidewall of the openings O' and the anchor structures 130 are also contemplated.

As indicated above, in one embodiment, the flowable material 150 which cures or sets to a non-flowable hardened state constitutes a bone cement or a bone paste. However, it should be understood that other suitable types of flowable materials that cure or set to a non-flowable hardened state are also contemplated for use in association with the femoral component 100. Additionally, the flowable material 150 may include bone growth promoting materials or substances such as bone graft material or bone morphogenic proteins (BMP), therapeutic materials or substances, or any other biocompatible materials or substances that would occur to one of skill in the art.

It should be understood that any experiments, experimental examples, or experimental results provided herein are intended to be illustrative of the present invention and should not be construed to limit or restrict the invention scope. Further, any theory, mechanism of operation, proof, or finding stated herein is meant to further enhance understanding of the present invention and is not intended to limit the present invention in any way to such theory, mechanism of operation, proof, or finding. In reading the claims, words such as "a", "an", "at least one", and "at least a portion" are not intended to limit the claims to only one item unless specifically stated to the contrary. Further, when the language "at least a portion" and/or "a portion" is used, the claims may include a portion and/or the entire item unless specifically stated to the contrary. Additionally, when the term "distal" is used with respect to a structure, the term refers to the far end of the structure, and when the term "proximal" is used with respect to a structure, the term refers to the near end of the structure.

Various changes and modifications to the described embodiments described herein will be apparent to those skilled in the art, and such changes and modifications can be made without departing from the spirit and scope of the invention and without diminishing its intended advantages. Additionally, while the invention has been illustrated and described in detail in the drawings and foregoing description, the same is to be considered illustrative and not restrictive in character, it being understood that only selected embodiments have been shown and described and that all changes, equivalents, and modifications that come within the scope of the inventions described herein or defined by the following claims are desired to be protected.

What is claimed is:

1. An orthopaedic implant including a femoral component of a knee prosthesis for installation onto an end portion of a femoral bone, comprising:

a base portion and anterior and posterior transverse portions extending transversely from said base portion to thereby define an inner region of the implant sized for receipt of the end portion of the femoral bone therein, wherein said anterior transverse portion defines a first inner bone interface surface that is tapered relative to a second inner bone interface surface defined by said posterior transverse portion, wherein said first inner bone interface surface defined by said anterior transverse portion inwardly converges relative to said second inner bone interface surface defined by said posterior transverse portion in a direction extending away from said base portion along an anatomic axis of the femoral bone; and at least one anchor structure projecting axially from said base portion and sized and configured for receipt within a substantially complementary opening formed in the end portion of the femoral bone, said anchor structure extending along a longitudinal axis and including a proximal end attached to said base portion and an opposite distal end, said anchor structure has a generally conical configuration including a tapered outer surface that inwardly tapers in a proximal-to-distal direction along said longitudinal axis, wherein said tapered outer surface of said anchor structure defines a concave curvature extending in a proximal-to-distal direction along said longitudinal axis, said concave curvature extending along at least two-thirds of an overall length of said anchor structure extending from said base portion, said concave curvature defining a varying taper angle relative to said longitudinal axis that decreases in a proximal-to-distal direction along said longitudinal axis.

2. The orthopaedic implant of claim 1, wherein said concave curvature extends substantially entirely along said tapered outer surface to said distal end of said anchor structure.

3. The orthopaedic implant of claim 1, wherein said anchor structure has a frustoconical shape.

4. The orthopaedic implant of claim 1, wherein said concave curvature extends along an arc having a varying radius of curvature.

5. The orthopaedic implant of claim 1, wherein said concave curvature extends to the distal end of said anchor structure.

6. The orthopaedic implant of claim 1, wherein said concave curvature extends along a concave surface radius that is larger than a maximum convex surface radius of said anchor structure measured from said longitudinal axis.

7. The orthopaedic implant of claim 1, wherein said tapered outer surface of said anchor structure defines a varying taper rate relative to said longitudinal axis that decreases in a proximal-to-distal direction along said longitudinal axis.

8. The orthopaedic implant of claim 7, wherein said concave curvature extends substantially entirely along said tapered outer surface to the distal end of said anchor structure.

9. The orthopaedic implant of claim 1, wherein said anterior transverse portion extends from a first end of said base portion, and wherein said posterior transverse portion extends from a second end of said base portion opposite said first end.

10. The orthopaedic implant of claim 1, wherein said first inner bone interface surface defined by said anterior transverse portion is planar and extends along a first plane, and wherein said second inner bone interface surface defined by said posterior transverse portion is planar and extends along a second plane that inwardly converges relative to said first plane in said direction extending away from said base portion.

11. The orthopaedic implant of claim 1, wherein said anchor structure includes a mount portion projecting from said base portion to said tapered outer surface.

12. The orthopaedic implant of claim 11, wherein said mount portion of said anchor structure includes a threaded stem configured for threading engagement within a threaded opening in said base portion.

13. The orthopaedic implant of claim 1, wherein said tapered outer surface of said anchor structure defines a varying taper rate relative to said longitudinal axis that decreases in a proximal-to-distal direction along said longitudinal axis, said varying taper rate extending along at least one-half of the overall length of said anchor structure.

14. The orthopaedic implant of claim 13, wherein said varying taper rate extends along at least two-thirds of the overall length of said anchor structure.

15. The orthopaedic implant of claim 1, further comprising a second of said anchor structure extending from one of said base portion and said anterior and posterior transverse portions, said second anchor structure sized and configured for receipt within a second opening formed in the end portion of the femoral bone.

16. The orthopaedic implant of claim 1, wherein said anchor structure includes one or more grooves extending into said tapered outer surface; and further comprising a flowable material positioned about at least a portion of said tapered outer surface and within said grooves, and wherein said flowable material is configured to cure to a hardened state.

17. The orthopaedic implant of claim 16, wherein said one or more grooves comprise a plurality of circumferential grooves extending about said tapered outer surface of said anchor structure.

18. The orthopaedic implant of claim 16, wherein said flowable material comprises a bone cement material.

19. An orthopaedic implant including a femoral component of a knee prosthesis for installation onto an end portion of a femoral bone, comprising:

a base portion and anterior and posterior transverse portions extending transversely from said base portion to thereby define an inner region of the implant sized for receipt of the end portion of the femoral bone therein, said anterior transverse portion defining a first inner bone interface surface that inwardly converges relative to a second inner bone interface surface defined by said posterior transverse portion in a direction extending away from said base portion along an anatomic axis of the femoral bone; and at least one anchor structure projecting axially from said base portion and sized and configured for receipt within a substantially complementary opening formed in the end portion of the femoral bone, said anchor structure extending along a longitudinal axis and including a proximal end attached to said base portion and an opposite distal end, wherein said anchor structure has a generally conical configuration, said anchor structure including a tapered outer surface defining a concave curvature extending generally along said longitudinal axis and inwardly tapering in a proximal-to-distal direction along said longitudinal axis, wherein said concave curvature extends along at least two-thirds of an overall length of said anchor structure extending from said base portion, said concave curvature defining a varying taper angle relative to said longitudinal axis that decreases in a proximal-to-distal direction along said longitudinal axis.

20. The orthopaedic implant of claim 19, wherein said concave curvature extends substantially entirely along said tapered outer surface to the distal end of said anchor structure.

21. The orthopaedic implant of claim 19, wherein said concave curvature defines a varying taper rate relative to said longitudinal axis that decreases in a proximal-to-distal direction along said longitudinal axis.

22. The orthopaedic implant of claim 19, wherein said concave curvature of said anchor structure extends to said distal end of said anchor structure.

23. The orthopaedic implant of claim 19, wherein said anchor structure includes one or more grooves extending into said tapered outer surface; and
   further comprising a flowable material positioned about at least a portion of said tapered outer surface and within said grooves, and wherein said flowable material is configured to cure to a hardened state.

24. The orthopaedic implant of claim 23, wherein said one or more grooves comprise a plurality of circumferential grooves extending about said tapered outer surface of said anchor structure.

25. The orthopaedic implant of claim 23, wherein said flowable material comprises a bone cement material.

26. The orthopaedic implant of claim 19, wherein said concave curvature extends along a concave surface radius that is larger than a maximum convex surface radius of said anchor structure measured from said longitudinal axis.

27. The orthopaedic implant of claim 19, further comprising a second of said anchor structure projecting from one of said base portion and said anterior and posterior transverse portions, said second anchor structure sized and configured for receipt within a second opening formed in the end portion of the femoral bone.

28. The orthopaedic implant of claim 19, wherein said anterior transverse portion extends from a first end of said base portion;
   wherein said posterior transverse portion extends from a second end of said base portion opposite said first end;
   wherein said first inner bone interface surface defined by said anterior transverse portion is planar and extends along a first plane; and
   wherein said second inner bone interface surface defined by said posterior transverse portion is planar and extends along a second plane that inwardly converges relative to said first plane in said direction extending away from said base portion.

29. The orthopaedic implant of claim 19, wherein said concave curvature extends along an arc having a varying radius of curvature.

30. A femoral implant component of a knee prosthesis for installation onto an end portion of a femoral bone, comprising:
   a base portion and anterior and posterior transverse portions extending transversely from said base portion to thereby define an inner region of the femoral implant component sized for receipt of the end portion of the femoral bone therein, wherein said anterior transverse portion defines a first inner bone interface surface that is tapered relative to a second inner bone interface surface defined by said posterior transverse portion, wherein said first inner bone interface surface defined by said anterior transverse portion inwardly converges relative to said second inner bone interface surface defined by said posterior transverse portion in a direction extending away from said base portion along an anatomic axis of the femoral bone; and
   at least one anchor peg projecting axially from said base portion and having a size and shape configured for receipt within a substantially complementary opening formed in the end portion of the femoral bone, said anchor peg extending along a longitudinal axis and including a proximal end attached to said base portion and an opposite distal end, said anchor peg having a generally conical configuration including a tapered outer surface that inwardly tapers in a proximal-to-distal direction along said longitudinal axis, wherein said tapered outer surface of said anchor peg defines a concave curvature that curves in a proximal-to-distal direction along said longitudinal axis, said concave curvature extending along at least two-thirds of an overall length of said anchor peg extending from said base portion, said concave curvature defining a varying taper angle relative to said longitudinal axis that decreases in a proximal-to-distal direction along said longitudinal axis.

* * * * *